United States Patent [19]

Tsuchihashi et al.

[11] 4,029,712

[45] June 14, 1977

[54] SULFOXIDE DERIVATIVE AND PROCESS FOR ITS PREPARATION

[75] Inventors: Genichi Tsuchihashi, Tama; Katsuyuki Ogura, Kyoto, both of Japan

[73] Assignee: Sagami Chemical Research Center, Tokyo, Japan

[22] Filed: Mar. 30, 1973

[21] Appl. No.: 347,408

Related U.S. Application Data

[62] Division of Ser. No. 211,100, Dec. 22, 1971, Pat. No. 3,742,066.

[30] Foreign Application Priority Data

Apr. 20, 1971 Japan .............................. 46-24908
May 11, 1971 Japan .............................. 46-30810

[52] U.S. Cl. ..................... 260/609 R; 260/607 AL; 260/609 E
[51] Int. Cl.² ........................................ C07C 149/14
[58] Field of Search ........ 260/607 A, 609 R, 909 B

[56] References Cited

UNITED STATES PATENTS 2,979,435  4/1961  Raasch .......................... 260/607 A

FOREIGN PATENTS OR APPLICATIONS 922,708  4/1963  United Kingdom ........... 260/607 A

*Primary Examiner*—Delbert R. Phillips
*Attorney, Agent, or Firm*—Wenderoth, Lind & Ponack

[57] ABSTRACT

A novel sulfoxide derivative of the general formula

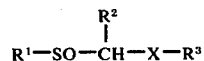

wherein $R^1$ and $R^3$ are the same or different, and each represents and alkyl group having 1 to 4 carbon atoms, a phenyl group or a halo- or methyl-substituted phenyl group, $R^2$ is a hydrogen atom, a lower alkyl group, benzyl group, or a p-methoxy- or p-bromo-benzyl group, $R^1$ and $R^2$, together, may form an alkylene group containing 3 carbon atoms, and X is an oxygen or sulfur atom, and to a process for its preparation.

2 Claims, No Drawings

SULFOXIDE DERIVATIVE AND PROCESS FOR ITS PREPARATION

This is a continuation, division, of application Ser. No. 211,100, filed Dec. 22, 1971, now U.S. Pat. No. 3,742,066.

This invention relates to a novel sulfoxide derivative of the general formula $$R^1-SO-\underset{\underset{R^2}{|}}{CH}-X-R^3$$

wherein $R^1$ and $R^3$ are the same or different, and each represents an alkyl group having 1 to 4 carbon atoms, a phenyl group or a halo- or methyl-substituted phenyl group, $R^2$ is a hydrogen atom, a lower alkyl group, benzyl group, or a p-methoxy- or p-bromobenzyl group, $R^1$ and $R^2$, together, may form an alkylene group containing 3 carbon atoms, and X is an oxygen or sulfur atom, and to a process for its preparation.

The novel sulfoxide has an fungicidal action, and is therefore useful as a fungicide. It can also be used as a material for the production of various medicines and agricultural chemicals. For instance, Dopa, i.e. 3-(3,4-dihydroxyphenyl)-L-alanine, and Pentazocine, i.e., 2'-hydroxy-5,9-dimethyl-3-(3-methyl-2-butenyl)-6,7-benzomorphan, are advantageously produced by using these sulfoxides as reactants. [Reference: K. Ogura and G. Tsuchihashi, Tetrahedron Lett. 3151 (1971).] Furthermore, the sulfoxides of the present invention can be readily converted to the corresponding sulfones by oxidation.

Examples of the sulfoxides of the invention include methoxymethyl methyl sulfoxide, ethoxymethyl methyl sulfoxide, isopropoxymethyl methyl sulfoxide, methyl phenoxymethyl sulfoxide, methyl phenylthiomethyl sulfoxide, t-butylthiomethyl phenyl sulfoxide, phenylthiomethyl phenyl sulfoxide, isopropylthiomethyl phenyl sulfoxide, p-chlorophenylthiomethyl phenyl sulfoxide, p-tolylthiomethyl phenyl sulfoxide, methyl methylthiomethyl sulfoxide, ethyl ethylthiomethyl sulfoxide, methylthiomethyl phenyl sulfoxide, methylthiomethyl p-tolyl sulfoxide, 1-methylthioethyl phenyl sulfoxide, alpha-methylthiobenzyl phenyl sulfoxide, isopropyl isopropylthiomethyl sulfoxide, p-chlorophenyl p-chlorophenylthiomethyl sulfoxide, methyl 1-methylthioethyl sulfoxide, methyl 2-(p-anisyl)-1-methylthioethyl sulfoxide, methyl 1-methylthio-2-phenylethyl sulfoxide, methyl 2-(p-bromphenyl)-1-methylthioethyl sulfoxide, methyl 1-methylthio-n-pentyl sulfoxide and trans-2-methylthiothiolane 1-oxide.

The novel sulfoxide of the present invention can be produced by reacting an alpha-halosulfoxide of the formula $$R^1-SO-\underset{\underset{R^2}{|}}{CH}-Hal \quad (I)$$

wherein $R^1$ and $R^2$ are defined above, and Hal is a halogen atom, with a compound of the formula $$R^3-XY \quad (II)$$

wherein $R^3$ and X are as defined above, and Y is a hydrogen atom or an alkali metal.

Specific examples of the alpha-halosulfoxide of the formula (I) include the following alpha-chlorosulfoxides and the corresponding alpha-bromosulfoxides: chloromethyl methyl sulfoxide, chloromethyl ethyl sulfoxide, chloromethyl isopropyl sulfoxide, chloromethyl t-butyl sulfoxide, chloromethyl phenyl sulfoxide, chloromethyl p-tolyl sulfoxide, chloromethyl p-chlorophenyl sulfoxide, alpha-chlorobenzyl methyl sulfoxide, alpha-chlorobenzyl methyl sulfoxide, alpha-chlorobenzyl phenyl sulfoxide, and cis-2-chlorothiolane 1-oxide.

Various methods of synthesizing these alpha-halosulfoxides have previously been known. One of them involves reacting p-toluene-sulfonyl chloride with methyl phenyl sulfoxide [M. Hojo and Z. Yoshida, J. Am. Chem. Soc., 90, 4496 (1968)]. More advantageous methods have been proposed by the inventors of the present application, and comprise halogenating a sulfoxide with N-chlorosuccinimide, sulfuryl chloride, chlorine, or bromine. [G. Tsuchihashi and K. Ogura, Bull, Chem. Soc. Japan, 44, 1726 (1971)); G. Tsuchihashi et al. Synthesis, 89 (1971); G. Tsuchihashi and S. Iriuchijima, Bull. Chem. Soc. Japan 43, 2271 (1970); S. Iriuchijima and G. Tsuchihashi, Synthesis 588 (1970)].

Examples of the compound of formula (II) are aliphatic alcohols such as methanol, ethanol, isopropanol and t-butanol; phenol; substituted phenols such as 4-methylphenol and 4-chlorophenol; aliphatic thiols such as methylmercaptan, ethylmercaptan, isopropylmercaptan and t-butylmercaptan; thiophenol; substituted thiophenols such as 4-methylthiophenol and 4-chlorothiophenol; and the alkali metal salts of all of these compounds. All of the compounds of formula (II) are produced or used as starting materials in the organic synthesis industry, and will be readily available.

The reaction of the alpha-halosulfoxide of formula (I) with the compound of formula (II) is shown by the following equation:

$$R^1-SO-\underset{\underset{R^2}{|}}{CH}-Hal + R^3-XY \longrightarrow$$

$$R^1-SO-\underset{\underset{R^2}{|}}{CH}-X-R^3 + Y-Hal.$$

It is advantageous that this reaction is conducted under the alkaline conditions. To maintain the alkaline conditions, an alkaline substance such as sodium hydroxide or potassium hydroxide may be added to the reaction system. When the compound of formula (II) to be used is in the form of an alkali metal salt as described above, it exhibits alkalinity by itself, and therefore it is not necessary to add an alkaline substance.

The reaction proceeds smoothly at ambient temperature. If desired, however, the rate of reaction can be accelerated by slow heating, say at a temperature below 100° C. The two reactants may be used in almost equimolar proportions. The use of a reaction medium is not altogether necessary, but advantageously, the reaction is performed in the presence of a solvent depending upon the kinds of the reactants and products. Solvents capable of dissolving the two reactants are preferred. Examples of the solvents useful in the present invention includes water, acetonitrile, dimethylformamide, dimethyl sulfoxide, and mixtures of these. Where the compound of formula (II) as a reactant is an alcohol and is used in excess, the excess portion will serve as the reaction medium.

Separately, by the present invention is provided a process for preparing a sulfoxide derivative of the general formula

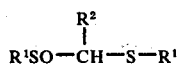

wherein $R^1$ is a lower alkyl group or a phenyl group, and $R^2$ is a hydrogen atom, a lower alkyl group, a benzyl group, or a p-methoxy- or p-bromobenzyl group, which comprises oxidizing a mercaptal of the general formula

wherein $R^1$ and $R^2$ have the above-identified meanings, with 1.0 – 3.0 oxidative equivalents of an oxidizing agent.

The mercaptals of said general formula (III) which can be used as the raw material for this process include both aliphatic and aromatic mercaptals such as acetaldehyde methylmercaptal, 1,1bis(methylthio)-2-(p-methoxyphenyl)-ethane, 1,1-bis(methylthio)-2-phenylethane, 1,1-bis(methylthio)-2-(p-bromophenyl)ethane, bis(ethylthio)methane, bis(isopropylthio)methane and bis(phenylthio)methane. These compounds can easily be prepared from mercaptans or thiophenols and formaldehyde which are comparatively cheap raw materials.

As the oxidizing agent of the present invention, substances which are generally used as oxidizing agents in organic chemical industries, such as hydrogen peroxide, m-chloroperbenzoic acid and sodium metaperiodate, may be used. In the process of the present invention, it is important to use the oxidizing agent in an amount within a certain range. Namely, it is important to use about 1 – 3 oxidative equivalents, based on the raw material compound, of oxidizing agent. In the case of less than about 1 equivalent, the amount of formation of the desired product is small, and in the case of more than about 3 equivalents, side reactions occur and this is not suitable in an industrial process. It is preferred to use about 1.5 – 2.5 oxidative equivalents. This oxidation reaction generally proceeds smoothly at a temperature of −20° C. to 50° C., but a temperature of −10° C. to room temperature is preferred since it does not require any special heating or cooling means. The use of a solvent is not essential, but acetic acid, methylene chloride, carbon tetrachloride, chloroform, alcohol, water, etc. may be used as solvent according to the type of the oxizing agent or the raw material compound.

The process of the present invention proceeds smoothly under the above-described conditions, and the desired sulfoxide having a sulfide bond in α-position can be produced selectively and with high yield. This separate process is particularly effective in case the terminal group connected with SO is the same as the terminal group connected with S.

The invention will be described by the following Examples in which the yield of the product is based on the alpha-halosulfoxide of formula (I) of the mercaptal of formula (III) used as the material.

EXAMPLE 1

Chloromethyl methyl sulfoxide (1.00g) was dissolved in 15 ml. of methanol, and 2.0g of potassium hydroxide was added to this mixture. The mixture was then heated at 50° C. for 18 hours. Chloroform (50 ml.) was then added, and the insoluble matter was removed by filtration. The filtrate was concentrated at reduced pressure, and then subjected to column-chromatography. There was obtained 720 mg of methoxymethyl methyl sulfoxide as a colorless liquid in a yield of 75%. A sample for analysis was prepared by purifying the product by distillation. The structure of the product was identified by infrared spectrum (IR), nuclear magnetic resonance spectrum (NMR), and mass spectrum.

| Product | |
|---|---|
| Boiling point: | 79° C./15 mmHg |
| IR (neat): | $\nu$so 1040 cm$^{-1}$ |
| | $\nu$C-O-C 1110 cm$^{-1}$ |
| NMR (CDCl$_3$): | δ4.40 s (2H), 3.65 s (3H), 2.57 s (3H) |
| Mass spectrum (12 ev): | M/e 108(M$^+$), 47.0 (base peak) |
| | No other conspicuous peak. |

The product was oxidized to the corresponding suflone, and its structure was identified.

| Melting point: | 25 – 26° C. |
|---|---|
| IR (neat): | 1306, 1285, 1125, 1100 cm$^{-1}$ |
| NMR (CDCl$_3$): | δ2.88 s (3H), 3.68 s (3H), 4.34 s (2H) |
| Elemental analysis for C$_3$H$_8$O$_3$S: | |
| Calculated: | C, 29.02; H, 6.50; S, 25.83 |
| Found: | C, 29.42; H, 6.38; S, 25.94 |

EXAMPLE 2

The procedure of Example 1 was repeated except using ethanol instead of methanol. There was obtained 816 mg of a colorless liquid having a boiling point of 80° – 82° C./5 mmHg in a yield of 76.5%. From IR, NMR and mass spectra, this product was identified as ethoxymethyl methyl sulfoxide.

| Product | |
|---|---|
| IR (neat): | $\nu$so 1038 cm$^{-1}$ |
| | $\nu$c-o-c 1110 cm$^{-1}$ |
| NMR (CDCl$_3$): | δ4.45 s (2H), 3.85 q (2H, J = 7.2 cps), 2.57 s (3H) |
| | 1.26 t (sH, J = 7.2 cps) |
| Mass spectrum (12 ev): | M/e 122 (M$^+$), 59 (base peak) |

The product was converted to the corresponding sulfone, and its structure was identified.

| Melting point: | 19 – 20.5° C. |
|---|---|
| IR (neat): | 1292, 1271, 1120, 1085 cm$^{-1}$ |
| NMR (CDCl$_3$): | δ1.36 t (3H, J = 9.0 Hz) |
| | 2.90 s (3H), 3.94 q (2H, J = 9.0 Hz), 4.42 s (2H) |
| Elemental analysis for C$_4$H$_{10}$O$_3$S: | |
| Calculated: | C, 34.77; H, 7.30 |
| Found: | C, 34.75; H, 7.31 |

EXAMPLE 3

The procedure of Example 1 was repeated except using isopropanol instead of methanol. There was obtained a colorless liquid having a boiling point of 71° C./7 mmHg in a yield of 55%. From IR, NMR and mass spectra, this product was identified as isopropoxymethyl methyl sulfoxide.

| Product | |
|---|---|
| IR (neat): | $\nu so$ 1035 cm$^{-1}$ |
| | $\nu c$-o-c 1102 cm$^{-1}$ |
| NMR (CCl$_4$): | $\delta 4.34$ s (2H), 3.97 septet (1H, J = 6 cps), 2.48 s (3H), 2.75 d (3H, J = 6 cps), 2.68 d (3H, J = 6 cps) |
| Mass spectrum (12 ev): | M/e 136 (M$^+$), 106 (8%)* 73 (58%), 64 (52%) 43 (base peak), 41 (15%) |
| *Intensity relative to the base peak | |
| Elemental analysis for C$_5$H$_{12}$O$_2$S: | |
| Calculated: | C, 44.09; H, 8.88; S, 23.54 |
| Found: | C, 43.71; H, 8.98; S, 23.41 |

EXAMPLE 4

Water (1 ml.) was added to a mixture of 707 mg of phenol and 904 mg of bromomethyl methyl sulfoxide, and then 580 mg of potassium hydroxide was dissolved in it in an atmosphere of nitrogen. The mixture was heated at 60° C. for 11.5 hours. Methylene chloride (40 ml.) was added, and the product was dried using anhydrous sodium sulfate, followed by concentration at reduced pressure. The product was subjected to column-chromatographyl [silica gel, chloroformethyl acetate (9 : 1)] to form 626 mg (yield 64.2%) of a colorless liquid having a boiling point of 131° C./2mmHg. From IR, NMR and mass spectra, this product was identified as phenoxymethyl methyl sulfoxide.

| Product | |
|---|---|
| IR (neat): | $\gamma so$ 1040 cm$^{-1}$ |
| | $\gamma c$-o-c 1202 cm$^{-1}$ |
| NMR (CCl$_4$): | $\delta 7.4 - 6.8$ m (5H), 4.95 d (1H, J = 9.5 cps), 2.58 s (3H) |
| Mass spectrum (70 ev): | M/e 170 (M$^+$), 107 (72%), 79 (25%), 77 (100%), 51 (29%) |

The corresponding sulfone

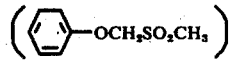

| Melting point: | 70 – 71° C. |
|---|---|
| IR (KBr): | 1299, 1131 cm$^{-1}$ |
| NMR (CDCl$_3$): | $\delta 2.99$ s (3H), 4.97 d (1H, J = 9.5 cps), 4.95 s (2H), 6.8 – 7.5 m (5H) |
| Elemental analysis for C$_8$H$_{10}$O$_3$S: | |
| Calculated: | C, 51.59; H, 5.41; S, 17.22 |
| Found: | C, 51.65; H, 5.69; S, 17.30 |

EXAMPLE 5

Potassium hydroxide (460 mg) was added in an atmosphere of nitrogen to a mixture of 560 mg of chloromethyl methyl sulfoxide and 616 mg of thiophenol, and then the mixture was heated at 60° C. for 13.5 hours. With addition of 3 ml. of water, the mixture was extracted with chloroform. The extract was dried using anhydrous sodium sulfate, and then subjected to column-chromatography [silica gel, chloroform-ethyl acetate (9 : 1)] to yield 812 mg of methyl phenylthiomethyl sulfoxide having a boiling point of 148° C./0.5 mmHg and an $n_D^{25}$ of 1.6053 as a colorless liquid in a yield of 87.3%.

| Elemental Analysis for C$_8$H$_{10}$S$_2$O | |
|---|---|
| Calculated: | C, 51.57; H, 5.41; S, 34.43 |
| Found: | C, 51.51; H, 5.75; S, 34.09 |

EXAMPLES 6 to 10

An alkali was added to a mixture of chloromethyl phenyl sulfoxide, thiol of various kinds, and 1 ml. of water, and the resultant mixture was heated at a predetermined temperature for a predetermined period of time in an atmosphere of argon. Methylene chloride (50 ml.) was added, the product was dried with anhydrous sodium sulfate. The product was subjected to column-chromatography (silica gel, methylene chloride). The reaction conditions and the results obtained are shown in Table 1 below.

Table 1

⟨◯⟩—SOCH$_2$Cl + R$^3$SH ⟶ ⟨◯⟩—SOCH$_2$SR$^3$
(I)                (II)

| Ex. | R$^3$ | Amount of compound (I) (mg) | Amount of compound (II) | Amount of KOH | Heating temperature (° C.) | Heating time (hr) | Yield (%) |
|---|---|---|---|---|---|---|---|
| 6 | t-Butyl | 830 | 2 ml | 1.0g | 50 | 18 | 80.0 |
| 7 | 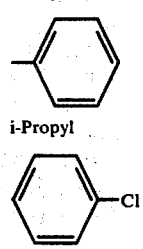 | 804 | 666 mg | 400 mg | 50 | 15 | 97.6 |
| 8 | i-Propyl | 1026 | 2 ml | 1.0g | 50 | 24 | 94.5 |
| 9 | ⟨◯⟩—Cl | 810 | 830 mg | 500 mg | 75 | 16.5 | 88.9 |

Table 1-continued $$\text{Ph-SOCH}_2\text{Cl} + R^3\text{SH} \longrightarrow \text{Ph-SOCH}_2\text{SR}^3$$
$$\phantom{xxxxx}(I)\phantom{xxxxxx}(II)$$

| Ex. | $R^3$ | Amount of compound (I) (mg) | Amount of compound (II) | Amount of KOH | Heating temperature (°C.) | Heating time (hr) | Yield (%) |
|---|---|---|---|---|---|---|---|
| 10 | (p-tolyl)-CH₃ | 823 | 917 mg | 500 mg | 50 | 35 | 99.9 |

The products obtained in Examples 6 to 10 and their properties are as follows:

Example 6:
t-butylthiomethyl phenyl sulfoxide a colorless oil: IR (film), 1042 cm$^{-1}$; NMR (CCl$_4$); $\delta$1.38 s (9H), 3.64 d (1H, J = 13.5 HZ); 3.77 d (1H, J = 13.5 HZ), 7.3 – 7.8 m (5H). Anal. Calcd for C$_{11}$H$_{16}$OS$_2$: C, 57.85; H, 7.06; S, 28.08. Found: C, 57.71; H, 7.00; S. 28.08.

Example 7:
phenylthiomethyl phenyl sulfoxide a colorless oil: IR (film), 1049, 745 and 690 cm$^{-1}$; NMR (CCl$_4$): $\delta$3.98 d (1H, J = 13.5 HZ); 4.03 d (iH, J = 13.5 HZ), 7.1 – 7.8 m (10H). Anal. Calcd. for C$_{13}$H$_{12}$OS$_2$: C, 62.87; H, 4.87; S, 25.82. Found: C, 62.78; H, 4.85; S, 25.87.

Example 8:
isopropylthiomethyl phenyl sulfoxide a colorless oil: IR (film), 1044 cm$^{-1}$; NMR (CCl$_4$): $\delta$2.27 d (6H, J = 6.8 HZ), 3.18 sectet (iH, J = 6.8 HZ), 3.71 s (2H), 7.3 – 7.8 m (5H). Anal. Calcd. for C$_{10}$H$_{14}$OS$_2$: C, 56.03; H, 6.58. Found: C, 56.12; H, 6.64.

Example 9:
p-chlorophenylthiomethyl phenyl sulfoxide colorless crystals. mp 70° –71°: IR (KB$_r$), 1040 cm$^{-1}$; NMR (CCl$_4$): $\delta$4.00 s (2H), 7.1 – 7.8 m (9H). Anal. Calcd. for C$_{13}$H$_{11}$OS$_2$Cl: C, 55.21; H, 3.92; S, 22.68. Found: C, 55.19; H, 4.02; S, 22.73.

Example 10:
p-tolylthiomethyl phenyl sulfoxide a colorless oil: IR (film), 1048 cm$^{-1}$; NMR (CCl$_4$): 2.30 s (3H), 3.91 d (1H, J = 13.5 HZ), 3.99 d (1H, J = 13.5 HZ), 6.9 – 7.7 m (9H). Anal. Calcd. for C$_{14}$H$_{14}$ OS$_2$: C, 64.08; H, 5.38. Found: C, 63.96; H, 5.45.

EXAMPLE 11

Chloromethyl methyl sulfoxide (607 mg) was added to 3 ml. of a 20% aqueous solution of sodium salt of methyl mercaptan to induce an exothermic reaction. To the reaction mixture was added 25 ml. of chloroform, and the product was dried with anhydrous sodium sulfate, followed by column-chromatography [silica gel, chloroform-ethyl acetate (1 : 1)] to yield 640 mg of a colorless liquid having a boiling point of 90° C./5 mmHg and an n$_D^{25}$ of 1.5172. From IR, NMR and mass spectra, the product was identified as methyl methylthiomethyl sulfoxide.

Elemental analysis for C$_3$H$_8$OS$_2$
Calculated: C, 29.00; H, 6.49
Found: C, 28.97; H, 6.78

EXAMPLE 12

Chloromethyl phenyl sulfoxide (270 mg) was dissolved in 3 ml. of acetonitrile, and with addition of 1 ml of a 20% aqueous solution of sodium salt of methyl mercaptan, and the mixture was heated at 60° C. for 80 minutes. Chloroform (30 ml.) was added to the reaction product, and the product was dried with anhydrous sodium sulfate followed by column-chromatography (silica gel, chloroform) to yield 273 mg of colorless crystals having a melting point of 61° – 61.5° C. From IR, NMR and mass spectra, the product was identified as methylthiomethyl phenyl sulfoxide.

Elemental analysis for C$_8$H$_{10}$S$_2$O
Calculated: C, 51.57; H, 5.41; S, 34.43
Found: C, 51.62; H, 5.47; S, 34.37

EXAMPLE 13

A mixture of 30.085 g of chloromethyl p-tolyl sulfoxide and 110 ml. of sodium salt of methyl mercaptan was dissolved in 210 ml. of acetonitrile, and the solution was stirred for 13 hours at 40° C. The reaction product was extracted with methylene chloride, dried with anhydrous sodium sulfate, and concentrated to yield 33.533 g of crude crystals of methylthiomethyl p-tolyl sulfoxide. The crude crystals were recrystallized from methanol and carbon tetrachloride-n-hexane to yield white crystals having a melting point of 60.0° to 61.0° C.

Elemental analysis for C$_9$H$_{12}$OS$_2$
Calculated: C, 53.96; H, 6.04; S, 32.02
Found: C, 53.93; H, 6.13; S, 32.15

EXAMPLE 14

832 mg of (1-bromoethyl) phenyl sulfoxide was dissolved in 1 ml. of acetonitrile, and with addition of 3.3 ml. of a 20% aqueous solution of sodium salt of methyl mercaptan, the mixture was heated at 40° C. for 10 hours. The product was extracted with 50 ml. of chloroform, and dried with anhydrous sodium sulfate. The solvent was removed at reduced pressure, and the product was separated by column-chromatography (silica gel, chloroform). There was obtained 170 mg of 1-methylthioethyl phenyl sulfoxide in a yield of 75.4%.

| Elemental analysis for $C_9H_{12}OS_2$ | |
|---|---|
| Calculated: | C, 53.96; H, 6.04 |
| Found: | C, 53.81; H, 6.22 |

EXAMPLE 15

220 mg of (alpha-chlorobenzyl) phenyl sulfoxide was dissolved in 5 ml. of acetonitrile, and with addition of 3 ml. of a 20% aqueous solution of sodium salt of methyl mercaptan, the mixture was stirred for four days at room temperature. Methylene chloride (50 ml.) was added, and the product was dried with anhydrous sodium sulfate. The solvent was removed at reduced pressure. The product was separated by column-chromatography (silica gel, chloroform). There was obtained (alpha-methylthiobenzyl) phenyl sulfoxide as colorless crystals having a melting point of 104° – 105° C. in a yield of 82.6%.

EXAMPLE 16

524 mg of cis-2-chlorothiolane 1-oxide was dissolved in 1 ml. of acetonitrile, and with addition of 1.5 ml. of a 20% aqueous solution of sodium salt of methyl mercaptan, the mixture was stirred for 4 hours at room temperature. Methylene chloride (50 ml.) was added, and the product was dried with anhydrous sodium sulfate to yield 158 mg of trans-2-methylthiothiolane 1-oxide having a boiling point of 90° C./0.1 mmHg as a colorless liquid in a yield of 56.7%.

| IR (neat): | 1033 cm$^{-1}$ |
|---|---|
| NMR (CCl$_4$): | $\delta 3.87$ q (1H, J = 3 and 7 HZ) |
| | 2.30 s (3H), 1.7 – 3.2 m (6H) |
| Elemental analysis for $C_5H_{10}S_2O$: | |
| Calculatee: | C, 39.96; H, 6.71 |
| Found: | C, 39.66; H, 6.83 |

EXAMPLE 17

The procedure of Example 8 was repeated except using 826 mg of chloromethyl isopropyl sulfoxide instead of the chloromethyl phenyl sulfoxide. There was obtained 962 mg of isopropyl isopropylthiomethyl sufloxide in a yield of 90.9%. The melting point was 39°–40° C.

| IR (neat): | 1048 cm$^{-1}$ |
|---|---|
| NMR (CDCl$_3$): | $\delta 1.28$ d (3H, J = 6.8 HZ), |
| | 1.32 d (3H, J = 6.8 HZ), |
| | 1.34 d (6H, J = 6.8 HZ), |
| | 2.7 – 3.6 m (2H), |
| | 3.68 s (2H) |

EXAMPLE 18

Water (1 ml.) was added to a mixture of 2 ml. of ethyl mercaptan and 885 mg of chloromethyl ethyl sulfoxide, and then 1.0 g of potassium hydroxide was dissolved in the mixture. The solution was heated for 15 hours at 50° C. Methylene chloride (50 ml.) was added, and the product was dried with anhydrous sodium sulfate, followed by distillation at reduced pressure. There was obtained 1011 mg of ethyl ethylthiomethyl sulfoxide having a boiling point of 95° – 97° C./2.5 mmHg as a colorless liquid in a yield of 95%.

| IR (neat): | 1042 cm$^{-1}$ |
|---|---|
| NMR (CDCl$_3$): | $\delta 1.32$ t (3H, J = 7.4 HZ), |
| | 1.36 t (3H, J = 7.4 HZ), |
| | 2.5 – 3.3 m (4H), |
| | 3.72 s (2H) |
| Elemental analysis for $C_5H_{12}OS_2$: | |
| Calculated: | C, 39.43; H, 7.94; S, 42.12 |
| Found: | C, 39.22; H, 8.00; S, 42.04 |

EXAMPLE 19

The procedure of Example 9 was repeated except using 970 mg of chloromethyl p-chlorophenyl sulfoxide instead of the chloromethyl phenyl sulfoxide. There was obtained 1633 mg of p-chlorophenyl p-chlorophenylthiomethyl sulfoxide in a yield of 90%.

| Colorless crystals, m.p. | 81 – 82° C. |
|---|---|
| IR (KBr): | 1036 cm$^{-1}$ |
| NMR (CDCl$_3$): | $\delta 4.12$ s (2H), 7.32 A$_2$B$_2$q (4H) |
| | 7.54 A$_2$B$_2$q (4H) |
| Analysis calculated for $C_{13}H_{10}OS_2Cl_2$: | C, 49.22; H, 3.18; S, 20.21 |
| Found: | C, 48.95; H, 3.31; S, 20.10 |

EXAMPLE 20

15 ml. of acetic acid was added to 2.486 g of bis(ethylthio)methane, 2.07 ml of an aqueous solution of hydrogen peroxide (concentration: 30%) was added thereto while cooling the mixture with ice, and then the resultant mixture was stirred for 2 hours at room temperature. After the acetic acid was neutralized, the mixture was dried with anhydrous sodium sulfate, and was concentrated under reduced pressure. On distilling the leaving under reduced pressure, 2.305 g of ethyl ethylthiomethyl sulfoxide having boiling point of 95° – 97° C./2.5 mmHg was obtained as a colorless liquid. The yield was 83%.

| IR (neat): | 1042 cm$^{-1}$ |
|---|---|
| NMR (in CDCl$_3$): | $\delta 1.32$ t (3H, J = 7.4 HZ), |
| | 1.36 t (3H, J = 7.4 HZ), |
| | 2.5 – 3.3 m (4H), |
| | 3.72 s (2H) |

EXAMPLE 21

871 mg of bis(ethylthio)methane was dissolved in 10 ml of methylene chloride, and then 1.382 g of m-chloroperbenzoic acid (80% active) was added thereto while cooling the mixture with ice. After 1.5 hours of stirring under cooling with ice, 500 mg of potassium carbonate was added thereto, and then subjected to filtration. After concentrating the filtrate under reduced pressure, it was separated by means of column-chromatography (florisil, methylene chloride), and thus 543 mg of ethyl ethylthiomethyl sulfoxide was obtained. The yield was 55.8%.

EXAMPLE 22

2.652 g of bis(ethylthio)methane was dissolved in 21 ml of a mixed solvent consisting of water and methanol (2 : 1), and then 4.11 g of sodium metaperiodate was added thereto while cooling the mixture with ice. After 1 hour of stirring under cooling with ice, the mixture was subjected to filtration, and then the filtrate was subjected to extraction with methylene chloride (4 times with 50 ml of the extracting agent). The extract was dried with anhydrous sodium sulfate, and after concentration under reduced pressure, it was separated by means of column-chromatography (silica gel, methylene chloride - ethyl acetate). Thus, 260 g of ethyl ethylthiomethyl sulfoxide was obtained. The yield was 8.8%.

EXAMPLE 23

15 ml of acetic acid was added to 4.324 g of bis(isopropylthio)methane, then 3.00 ml of an aqueous solution of hydrogen peroxide (concentration: 3C %) was added thereto while cooling the mixture with ice, and then the resultant mixture was stirred for 4.5 hours at room temperature. 100 ml of methylene chloride and 18 g of potassium carbonate were added thereto, and after stirring, the mixture was subjected to filtration. On distilling the filtrate under reduced pressure, 3.606 g of isopropyl (isopropylthiomethyl) sulfoxide having a boiling point of 87° – 88° C./1 mmHg was obtained as colorless crystals. The melting point was 39° – 40° C.

| | |
|---|---|
| IR (neat): | 1048 cm$^{-1}$ |
| NMR (in CDCl$_3$): | $\delta$ 8.28 d (3H, J = 6.8 HZ), |
| | 1.32 d (3H, J = 6.8 HZ), |
| | 1.34 d (6H, J = 6.8 HZ), |
| | 2.7 – 3.6 m (2H), |
| | 3.68 s (2H) |
| Analysis as C$_7$H$_{16}$OS$_2$: | |
| Calculated: | C, 46.62; H, 8.92; S, 35.56 |
| Found: | C, 46.51; H, 9.00; S, 35.76 |

EXAMPLE 24

5 ml of acetic acid was added to 1.538 g of bis(phenylthio)methane, 0.75 ml of an aqueous solution of hydrogen peroxide (concentration: 30%) was added thereto, and then the mixture was stirred for 1 hour at room temperature. After 100 ml of methylene chloride, 6 g of potassium carbonate and a small amount of water were thereto, the resultant mixture was dried with anhydrous sodium sulfate. The product was concentrated under reduced pressure, and then the leavings were separated by means of column-chromatography (silica gel, methylene chloride). Thus 1.585 g of phenyl phenylthiomethyl sulfoxide was obtained as a colorless liquid. The yield was 96.6%.

| | |
|---|---|
| IR (neat): | 1049, 745, 690 cm$^{-1}$ |
| NMR (in CCl$_4$): | $\delta$ 3.98 d (1H, J = 13.5 HZ), |
| | 4.03 d (1H, J = 13.5 HZ), |
| | 7.1 – 7.8 (10H) |
| Analysis as C$_{13}$H$_{12}$OS$_2$: | |
| Calculated: | C, 62.87; H, 4.87; S, 25.82 |
| Found: | C, 62.78; H, 4.85; S, 25.87 |

EXAMPLE 25

5 ml of acetic acid was added to 1.255 g of bis(methylthio)methane, and then 1.32 ml of an aqueous solution of hydrogen peroxide (concentration: 30%) was added thereto while cooling the mixture with ice. After 2.5 hours of stirring under cooling with ice, the mixture was dried with anhydrous sodium sulfate. After concentration under reduced pressure, the mixture was separated by means of column-chromatography (silica gel, methylene chloride - ethyl acetate). Thus, 1.046 g of methyl methylthiomethyl sulfoxide was obtained. the yield was 72.5%. The product was identified with the standard substance by means of IR and TLC.

EXAMPLE 26

4.72 g of acetaldehyde methylmercaptal was dissolved in 10 ml of acetic acid, and then 4.05 ml of an aqueous solution of hydrogen peroxide (concentration: 30%) was added dropwise thereto while cooling the mixture with ice. Methylene chloride was added thereto, acetic acid was neutralized with potassium carbonate, and then the mixture was subjected to filtration. The filtrate was dried with anhydrous sodium sulfate, and then on distilling the product under reduced pressure, 3.62 g of methyl 1-methylthioethyl sulfoxide having a boiling point of 84° C./2 mmHg was obtained as a colorless liquid. The yield was 67.8%.

| | |
|---|---|
| Analysis as C$_4$H$_{10}$OS$_2$: | |
| Calculated: | C, 34.75; H, 7.29 |
| Found: | C, 34.36; H, 7.44 |

EXAMPLE 27

The same procedure as in Example 26 was followed except that 12.71 g of 1,1-bis-methylthio-2-(p-methoxyphenyl) ethane was used in place of 4.72 g of acetaldehyde methyl mercaptal, and thus 8.12 g of methyl 2-(p-anisyl)-1-methylthioethyl sulfoxide was obtained. The yield was 60.4%.

The results of IR and NMR show that this product is a 1 : 1 mixture of two types of diastereomers.

| | |
|---|---|
| IR (film): | $\nu$so 1037 cm$^{-1}$ |
| NMR (CDCl$_3$): | 7.05 A$_2$B$_2$q (4H), 3.81 s (3H), |
| | 3.8 – 2.2 m (3H), 2.74 s (3/2H), |
| | 2.61 s (3/2H), 2.17 s (3/2H), |
| | 2.14 s (3/2H) |
| Analysis as C$_{11}$H$_{16}$O$_2$S$_2$: | |
| Calculated: | C, 54.09; H, 6.55 |
| Found: | C, 53.98; H, 6.74 |

EXAMPLE 28

The same procedure as in Example 26 was followed, except that 7.98 g of 1,1-bis-methylthio-2-phenylethane was used in place of 4.72 g of acetaldehyde methyl mercaptal, and thus 6.55 g of methyl 1-methylthio-2-phenylethyl sulfoxide was obtained. The yield was 76.4%.

The results of NMR have clarified that this product is a 1 : 1 mixture of two types of diastereomers.

| | |
|---|---|
| NMR (CCl$_4$): | $\delta$7.22 s (5H), 3.8 – 2.2 m (3H), |
| | 2.63 s (3/2H), 2.48 s (3/2H), |
| | 2.14 s (3/2H), 2.09 s (3/2H) |
| Analysis as C$_{10}$H$_{14}$OS$_2$: | |
| Calculated: | C, 56.07; H, 6.55 |
| Found: | C, 56.01; H, 6.70 |

EXAMPLE 29

The same procedure as in Example 26 was followed except that 10.75 g of 1,1-bis(methylthio)-2-(p-bromophenyl)ethane was used in place of 4.72 g of acetaldehyde methyl mercaptal, and thus 7.75 g of methyl 2-(p-bromphenyl)-1-methylthioethyl sulfoxide was obtained. The yield was 68.2%.

NMR (CDCl₃): δ7.32 A₂B₂q (4H),
3.8 – 2.2 m (3H),
2.77 s (3H), 2.13 s (3H)

Analysis as C₁₆H₁₂OS₂BR:
Calculated: C, 40.97; H, 4.44
Found: C, 40.75; H, 4.73

EXAMPLE 30

The same procedure as in Example 26 was followed except that 6.40 g of 1,1-bis(methylthio)-n-pentane was used in place of 4.72 g of acetaldehyde methyl mercaptal, and thus 45.1 g of methyl 1-methylthio-n-pentyl sulfoxide was obtained. The yield was 63.4%.

Analysis as C₇H₁₆OS₂:
Calculated: C, 46.67; H, 8.89
Found: C, 46.59; H, 8.95 with suspension of conidia (containing 15 – 20 spores within a field of vision of an Olympus microscope of 600 magnifications) of Cladosporium Cucumerium Ellis et Arthur formed by culturing in a V-8 juice culture medium**. After the inoculated leaves were kept for one day in an inoculation box maintained at a temperature of 23° C. and a humidity of 100%, the pot was transferred again to the glass-house and was left as it was. The investigation was conducted 5 days after the inoculation of the germs, and the effect of the tested compound was judged in accordance with the following scale.

| | |
|---|---|
| 0 | No disease spot. |
| 1 | The area of disease spots is less than 10 % based on the total area of the leaves. |
| 2 | 10 to 50 %. |
| 3 | 50 to 90 %. |
| 4 | 90 to 100 %. |

The test results were as shown below:

| Tested compound | Time of inoculation | Preventive effect | Medicinal harm |
|---|---|---|---|
| Cl—C₆H₄—S(O)—CH₂—S—C₆H₄—Cl | 1 day after | 1 | none |
|  | 4 day after | 2 | none |
| Cl—C₆H₄—S(O)—CH₂—S—C₆H₄—CH₃ | 4 day after | 1 | none |
| CH₃—C₆H₄—S(O)—CH₂—S—C₆H₄—Cl | 1 day after | 0 | none |
| C₆H₅—S(O)—CH₂—S—C₆H₅ | 4 day after | 0 | none |
| CH₃—S(O)—CH₂—S—CH₃ | 1 day after | 1 | none |
|  | 4 day after | 1 | none |
| Control | 1 day after | 4 |  |
|  | 4 day after | 4 |  |

*Composition of the emulsion
Tested compound: 200 mg.
Xylene: 50 mg.
Sorpol-2680: 50 mg.
Sorpol-2680 is a mixture of polyoxyethylene phenylphenol polymer, polyoxyethylene sorbitan alkylate and polyoxyethylene alkylaryl ether.
**V-8 juice culture medium
V-8 juice 354 ml
(V-8 vegetable juice made by Campbell Soup Co., U.S.A.)
Calcium carbonate 5.3 g
Agar-agar 28.3 g

EXAMPLE 31

Test on the prevention of cucumber scab.

The seed of a cucumber (Shimoshirazu Jibai, a Japanese variety) was sown and raised in an unglazed pottery pot having a diameter of 15 cm in a glass-house, and when 4 full leaves were developed, they were sprayed with an aqueous emulsion containing 1,000 ppm (as effective ingredient concentration) of an emulsion* having the later-described composition by means of a spray gun to such an extent that the cucumber leaves were fully wetted. The wetted leaves were left as they were in the glass-house, and 1 day or 4 days after the spraying, they were inoculated by spraying Water is added to the above mixture to make its total volume 1770 ml, and after dissolving the ingredients by heating, the product was poured into dishes, and was left to cool and solidify therein.

What we claim is:
1. A process for preparing a sulfoxide derivative of the formula

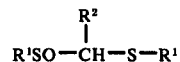

wherein R¹ is lower alkyl or phenyl and R² is hydrogen, lower alkyl, benzyl, p-methoxybenzyl or p-bromobenzyl, which comprises oxidizing a mercaptal of the formula

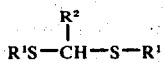

wherein R¹ and R² are as defined above, with 1.0–3.0 oxidative-equivalents of an oxidant selected from the group consisting of hydrogen peroxide, m-chloroperbenzoic acid and sodium metaperiodate at a temperature of from −20° to 50° C.

2. A process according to claim 1, wherein an oxidant is hydrogen peroxide.

* * * * *